United States Patent [19]

Ishida et al.

[11] Patent Number: 5,202,250

[45] Date of Patent: Apr. 13, 1993

[54] METHOD FOR ISOLATION AND PURIFICATION OF AMYLASES, AND ADSORBENTS USED FOR THE SAME AS WELL AS DEVICES FOR THE ISOLATION AND PURIFICATION

[75] Inventors: Masahiko Ishida; Ryoichi Haga; Yuusaku Nishimura, all of Hitachi; Masami Satoh, Ibaraki, all of Japan

[73] Assignee: Hitachi, Ltd., Tokyo, Japan

[21] Appl. No.: 104,984

[22] Filed: Oct. 6, 1987

[30] Foreign Application Priority Data

Oct. 6, 1986 [JP] Japan .................... 61-236147

[51] Int. Cl.$^5$ .................... C12N 9/26; C12N 9/28; C12N 9/30; B01J 20/00
[52] U.S. Cl. .................... 435/201; 435/202; 435/203; 435/204; 435/205; 435/209; 435/211; 502/404
[58] Field of Search ............... 435/201, 202, 203, 204, 435/205, 209, 211; 536/1.1, 106, 112, 120; 502/404; 527/300

[56] References Cited

U.S. PATENT DOCUMENTS

| | | | |
|---|---|---|---|
| 3,002,823 | 10/1961 | Flodin et al. | 536/112 |
| 3,525,672 | 8/1970 | Wurzburg et al. | 435/96 |
| 4,460,683 | 7/1984 | Gloger et al. | 435/10 |
| 4,639,423 | 1/1987 | Kahlert et al. | 435/287 |

FOREIGN PATENT DOCUMENTS

| | | |
|---|---|---|
| 57-063303 | 4/1982 | Japan . |
| 84741 | 9/1984 | Romania . |
| 8503509 | of 0000 | World Int. Prop. O. . |

OTHER PUBLICATIONS

Serban et al., Rev. Roum. Biochim. 21(3), 219–25, 1984 (CA 102:2605z).
Serban et al., Rev. Roum. Biochim. 23(4), 319–24, 1986 (CA 106:115915b).
DeMot et al., Eur. J. Biochem., 164(3), 643–54, 1987.
Zemak et al., Biopolymers, 18(9), 2135–44, 1979.
Marshall et al., Carbohydrate Research, vol. 61, pp. 407–417, 1978.
Analytical Letters, vol. 14 (B17, 18) 1981, pp. 1501–1514 New York, US H. D. Schell, et al "Alpha Amylase purific. and separation from glucoamylase by affinity chromato. on cross-linked amylase (CL-amylase)"—in part. p. 1510.
Enzyme Microb. Technol. vol. 5, May 1983, pp. 196–198 JP; S. Ueda, et al "Behaviour of Endomycopsis fibuligera glucoamylase towards raw starch".

Primary Examiner—Douglas W. Robinson
Assistant Examiner—L. Blaine Lankford
Attorney, Agent, or Firm—Antonelli, Terry, Stout & Kraus

[57] ABSTRACT

Cross-linked polyglucans obtained by cross-linking polyglucans having branched chains intermolecularly and/or intramolecularly or cross-linked homooligomers obtained by cross-linking α-1,4-linked homooligomers of glucose intermolecularly can selectively adsorb glucoamylase and/or β-amylase thereto. By the use of such three-dimensional, cross-linked high molecular weight substances, glucoamylase and β-amylase can be isolated and purified extremely efficiently.

3 Claims, 6 Drawing Sheets

METHOD FOR ISOLATION AND PURIFICATION OF AMYLASES, AND ADSORBENTS USED FOR THE SAME AS WELL AS DEVICES FOR THE ISOLATION AND PURIFICATION

BACKGROUND OF THE INVENTION

1. Field of the Invention

The present invention relates to a method for isolation and purification of amylases, and adsorbents used for the same as well as devices for the isolation and purification. More particularly, the present invention relates to cross-linked polyglucans or cross-linked glucose homooligomers suited for adsorbing glucoamylases and β-amylase with high selectivity and a method for isolation and purification of amylases using them as well as devices for the method.

2. Related Art Statement

Glucose, isomerized glucose and maltose are currently produced industrially by hydrolysis of starches using α-amylase, glucoamylase or β-amylase.

As such, glucoamylase and β-amylase are extremely useful for industrially producing useful low molecular sweeteners from starches.

In general, enzymes are prepared by liquid culture of microorganisms capable of producing the enzymes, namely, enzyme-producing bacteria. Enzymes as reagents for research have been used after partial purification or purification to a high degree, by complicated processes for isolation and purification, in combination with salting out, ion exchange chromatography, electrophoresis, etc.

On the other hand, preparations of enzyme for industrial use are obtained as concentrates of culture filtrates concentrated as they are, or dry powders, or concentrates obtained by isolation and purification of the filtrates or dry powders of the concentrates.

However, the concentrates of culture filtrates or crude dry products contain large quantities of components of unpleasant odor or colored components which are contained in the culture filtrates. Therefore, upon isolation and purification of the desired reaction product, it is necessary to finally remove these components. Further in many cases, culture filtrates also contain proteases. In crude enzyme solutions such as culture filtrates or the like, which contain proteases in addition to amylases, the amylases are often decomposed and inactivated by the action of proteases, during the course of purification or upon progress of the desired reaction. For this reason, it is necessary to remove these unfavorable impurities, in producing useful materials utilizing reactions of enzymes such as amylases.

Thus, a heavy burden is loaded on steps of isolation and purification for products in subsequent reactions.

On the other hand, salting out and liquid chromatography which are known to be conventional methods for purification have a limit that is partial concentration. In order to enhance accuracy of isolation, these operational conditions, for example, kind of precipitating agent, concentration, pH, kind of filler, kind of adsorbent and desorbent, or the like, must be changed, and complicated processes in combination with these conditions must be used.

Moreover, the operations involve addition of salts in large quantities as precipitating agents or eluting agents, which also necessitates desalting operations upon subjecting to a subsequent step. Further, with respect to BOD wastes showing a salt concentration as high as several 10% which generate during the course of such purification steps, it is not so simple to treat the wastes.

From the foregoing, known methods for purification comprising these complicated steps are limited mainly to purification of reagents or the like for research use.

If there is developed an adsorbent capable of selectively adsorbing glucoamylase and β-amylase known to be particularly difficult to be purified, irrespective of difference in structure of enzyme molecule due to difference in origin of enzyme, both enzymes could be concentrated and isolated from culture solutions at one step in a high purity.

Paying attention to the adsorption method using amylose (linear polymer of glucose, molecular weight of 100,000 to 400,000, number of glucose polymerized: $5 \times 10^2$ to $2 \times 10^3$) as an adsorbent that is known to be a method of purification of α-amylase, the present inventors have attempted to apply the adsorption method to glucoamylase and α-amylase. However, its adsorption capacity is as extremely low as $1/10^3$ or less, as compared to the case of α-amylase. It is thus understood that the known method using amylose as an adsorbent is not practical for purification of glucoamylase and β-amylase.

SUMMARY OF THE INVENTION

An object of the present invention is to provide adsorbents which can efficiently adsorb a desired amylase thereto highly selectively from enzyme-containing liquid containing many and various kinds of impurities other than glucoamylase and β-amylase.

Another object of the present invention is to provide adsorbents which can form a complex, upon contact with an aqueous solution of glucoamylase or β-amylase, in which these amylases become a gel insoluble in water so that glucoamylase or β-amylase can be isolated and purified extremely easily.

A further object of the present invention is to provide novel cross-linked polyglucans and novel cross-linked homooligomers which can efficiently adsorb and isolate glucoamylase or β-amylase highly selectively.

A still further object of the present invention is to provide processes of producing cross-linked polyglucans and cross-linked homooligomers.

A still further object of the present invention is to provide a method for isolation and purification of amylases using cross-linked polyglucans or cross-linked homooligomers which can efficiently adsorb and isolate a desired amylase highly selectively from enzyme-containing liquid containing many and various kinds of impurities, in addition to glucoamylase and β-amylase.

A still further object of the present invention is to provide a method for isolation and purification of amylases in which enzyme-containing liquid is brought into contact with novel adsorbents that can selectively adsorb one or both of glucoamylase and β-amylase thereby to adsorb and isolate one or both of the enzymes.

A still further object of the present invention is to provide a method for readily desorbing glucoamylase and β-amylase adsorbed to the adsorbents.

A still further object of the present invention is to provide devices for isolation and purification of amylases which can efficiently adsorb and isolate glucoamylase and β-amylase highly selectively.

These and other objects and advantages of the present invention will be apparent from the following description.

A first aspect of the present invention relates to three-dimensionally cross-linked high molecular weight substances (cross-linked polyglucans) which can be obtained by cross-linking polyglucans having branched chains intermolecularly and/or intramolecularly.

A second aspect of the present invention relates to three-dimensionally cross-linked high molecular weight substances (cross-linked homooligomers) which can be obtained by cross-linking α-1,4-linked homooligomers of glucose intermolecularly.

A third aspect of the present invention relates to a method for isolation and purification of amylases which comprises:

a step of contacting a crude enzyme aqueous solution containing one or both of glucoamylase and β-amylase with one or both of three-dimensionally cross-linked high molecular weight substances, which are obtained by cross-linking polyglucans having branched chains intermolecularly and/or intramolecularly or by cross-linking α-1,4-linked homooligomers of glucose inter-molecularly, thereby to adsorb one or both of glucoamylase and β-amylase;

a step of isolating from the solution a hydrated gel of the three-dimensionally cross-linked high molecular weight substances to which the amylase has been adsorbed; and, a step of contacting the hydrated gel with any of a weakly alkaline aqueous solution, an aqueous salt solution of at least 0.5M and an aqueous solution which is weakly alkaline and contains a salt, to desorb the adsorbed amylases.

A fourth aspect of the present invention relates to a process of producing cross-linked polyglucans or cross-linked homooligomers which comprises cross-linking polyglucans having branched chains or α-1,4-linked homooligomers of glucose to such a degree that a solubility in water becomes 0.01% or less at 60° C.

A fifth aspect of the present invention relates to devices for isolation and purification of amylases comprising:

a cell-free culture solution storage tank for storing crude enzyme aqueous solutions containing one or both of glucoamylase and β-amylase; and, an amylase adsorption tank for contacting the crude enzyme aqueous solutions with cross-linked polyglucans obtained by cross-linking polyglucans having branched chains intermolecularly and/or intramolecularly or with cross-linked homooligomers obtained by cross-linking α-1,4-linked homooligomers of glucose intermolecularly, having connected with the storage tank.

DETAILED DESCRIPTION OF THE INVENTION

Preferred adsorbents used in the present invention are shown below.

(a) Three-dimensionally cross-linked high molecular weight substances (cross-linked polyglucans) obtained by intermolecularly and/or intramolecularly cross-linking branched polyglucans, which have branched chains having non-reducing terminal glucose residues as open ends and polymerized through α-1,4-linkage of glucose, on the skeleton chain of glucose polymerized through α-1,4-linkage and, which are branched through α1,6-linkage in such a branching degree that the glucose residues corresponding to branching points in the skeleton chain amount to at least 5% of the total number of glucose residues in the molecule of the branched polyglucan.

A mean polymerization degree of the branched chains is 2 to 50, preferably 2 to 20.

Figure 1:
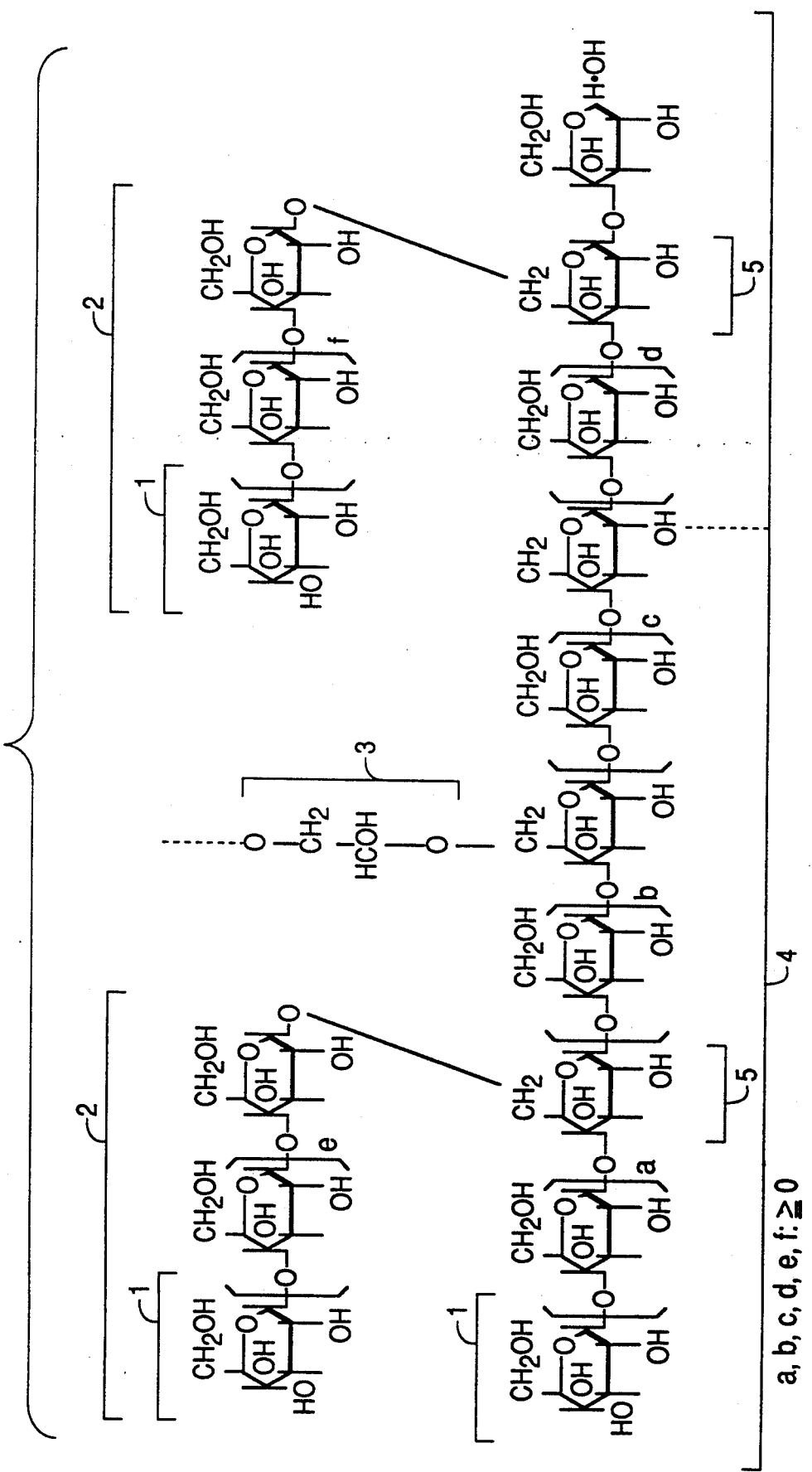
FIG. 1 shows a representative example of a structural unit for cross-linked polyglucan obtained using an epihalohydrin as a cross-linking agent.

A representative example of a structural unit of the substances obtained using an epihalohydrin as a cross-linking agent is shown in FIG. 1.

(b) Three-dimensionally cross-linked high molecular weight substances (cross-linked polyglucans) obtained by acting amylases, in particular, glucoamylase, β-amylase or α-amylase, on the branched polyglucans prior to cross-linking described in (a) thereby to shorten the polymerization number of glucose in the branched chains to from 2 to 6 and cross-linking the thus obtained branched polyglucans.

Such cross-linked polyglucans correspond to those shown in FIG. 1 wherein e and f are 0 to 4.

(c) Three-dimensionally cross-linked high molecular weight substances (cross-linked homooligomers) obtained by intermolecularly cross-linking homooligomers in which 2 to 50 glucose molecules are linearly polymerized through α-1,4-linkage.

Figure 2:
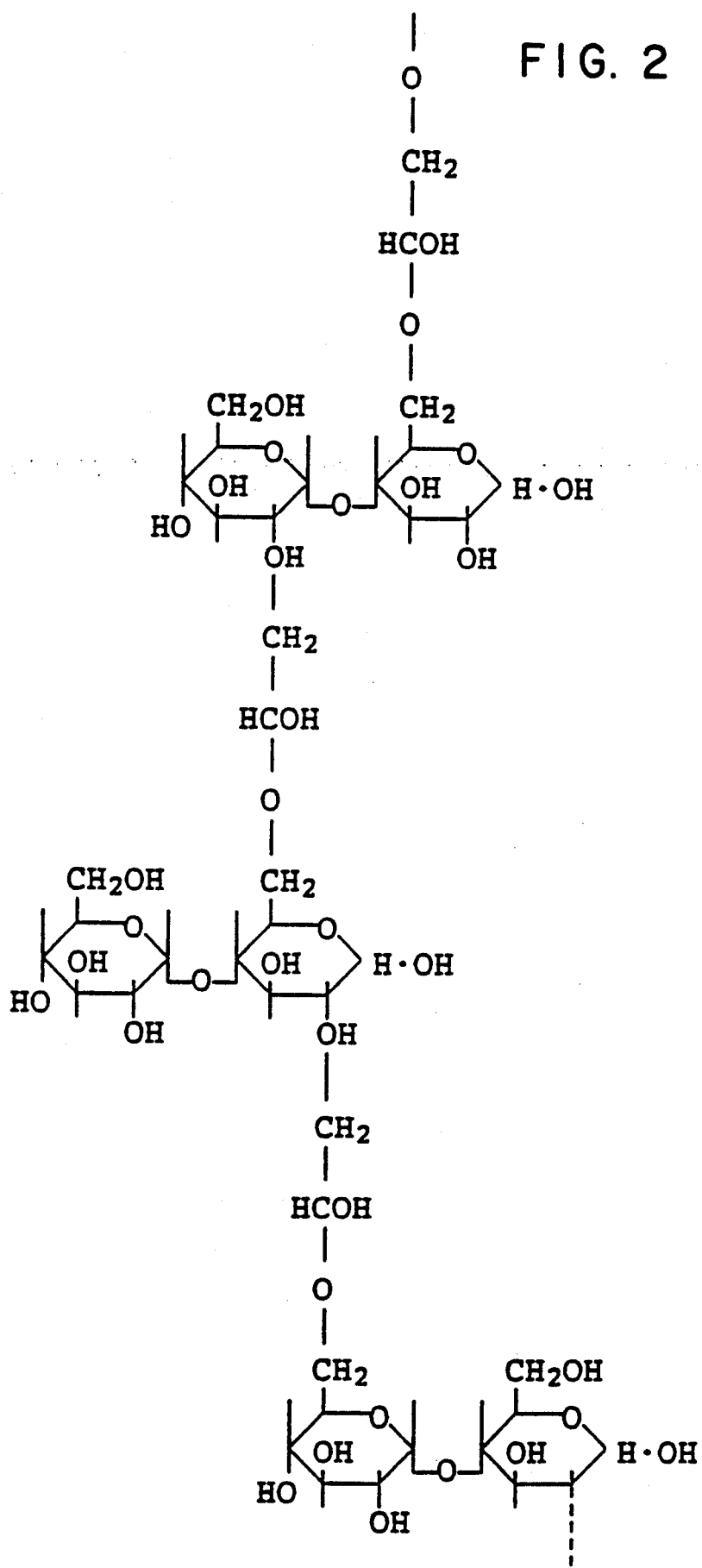
FIGS. 2 and 3 show representative examples of structural units for cross-linked homooligomers, obtained using epihalohydrins as cross-linking agents.
Figure 3:
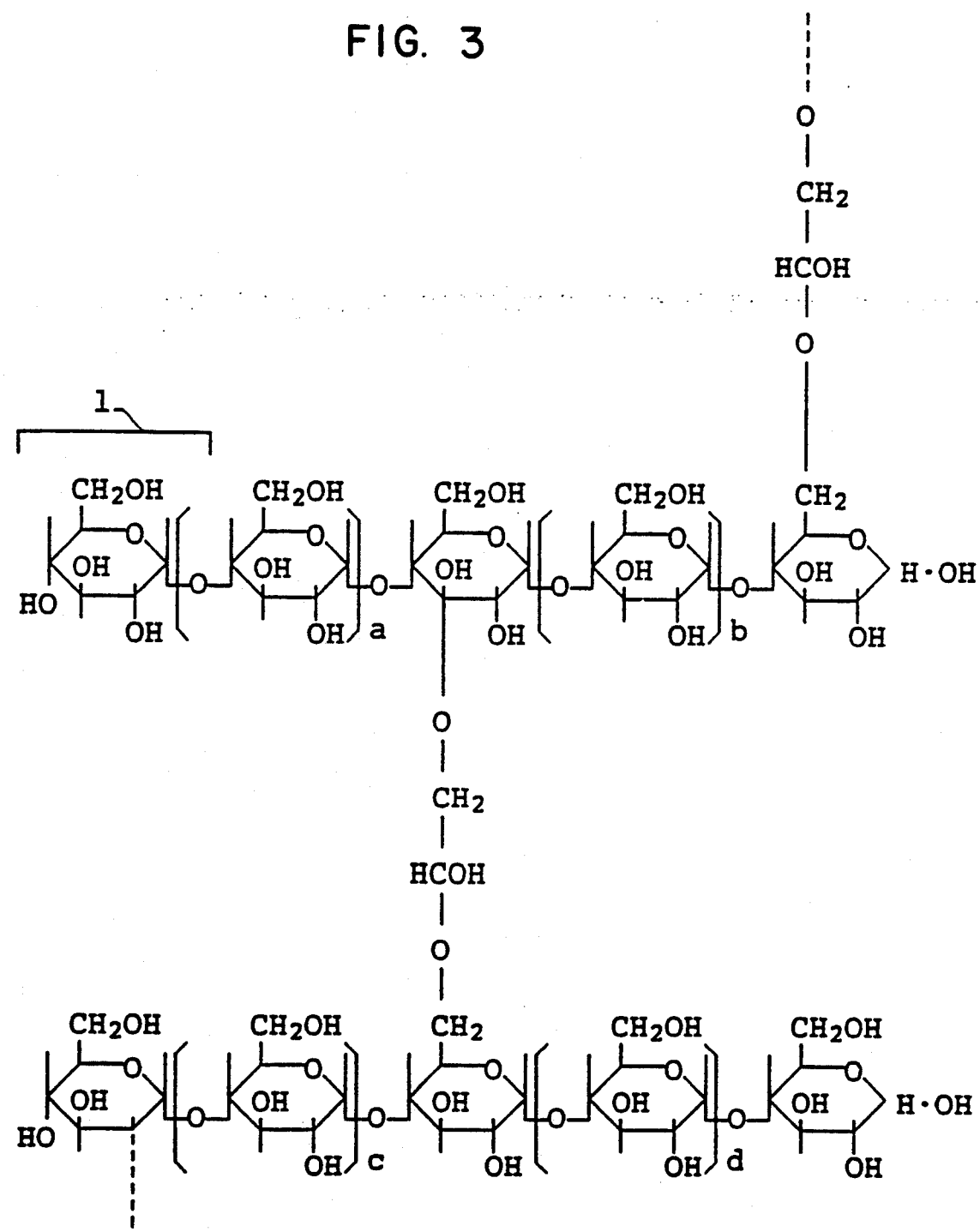

Representative examples of structural units of the substances obtained using epihalohydrins as cross-linking agents are shown in FIGS. 2 and 3.

The adsorbents used in the present invention do not substantially adsorb α-amylase thereto, so that glucoamylase and/or β-amylase can be substantially isolated from α-amylase.

By controlling the length of branched chains of cross-linked polyglucans which are adsorbents used in the present invention or, by controlling the chain length of homooligomers used for production of the cross-linked homooligomers, glucoamylase and β-amylase can be separated from each other. Namely, glucoamylase can be adsorbed to the adsorbent more selectively than β-amylase, by shortening the length of the branched chains or the homooligomer, that is, by adjusting a mean polymerization degree of glucose in the branched chains of cross-linked polyglucans to from 2 to 6, preferably from 2 to less than 4; or, by adjusting a mean polymerization degree of glucose in homooligomers used for production of cross-linked homooligomers to from 2 to 6, preferably 2 to less than 4. As the adsorbents used in the above procedure, there are preferred a cross-linked polyglucan obtained from glycogen or amylopectin treated with amylase, and a cross-linked homooligomer from maltose or maltotriose.

Further when the length of the branched chains or the homooligomer is made longer, namely, when cross-linked polyglucans having a mean polymerization degree of the branched chain of from 4 to 50, preferably 4 to 20, or cross-linked homooligomers obtained from homooligomer having a mean polymerization degree of 4 to 50, preferably 4 to 20, are used, both of glucoamylase and β-amylase can be adsorbed simultaneously. As the adsorbents used in the above procedure, there are preferred a cross-linked polyglucan obtained from glycogen or amylopectin, and a cross-linked homooligomer from maltotetraose or maltohexose.

The glucoamylase and β-amylase adsorbed to the adsorbents can be easily desorbed with a weakly alkaline aqueous solution, an aqueous solution of a salt having a concentration of at least 0.5M or an aqueous solution which is weakly alkaline and contains a salt.

Upon the adsorption and desorption of glucoamylase and β-amylase, it is preferred that the operation be conducted at temperatures of at or above a freezing point and within such a range that hydrolysis does not substantially occur.

The reasons are that the adsorbents used in the present invention also include those having such a structure that undergoes hydrolysis by glucoamylase, β-amylase or other glucanases contained in the crude enzyme solution and that consideration should also be made on decomposition of desired enzymes (glucoamylase and β-amylase) by proteases which might be contained in the crude enzyme solution and on thermostability of the desired enzymes.

By connecting the adsorption and desorption operations of the crude enzyme solution containing amylases performed by different kinds of adsorbents, the amylases, i.e., glucoamylase and β-amylase can be isolated, respectively.

For example, in the case of using a crude enzyme solution containing α-amylase, β-amylase and glucoamylase as a sample solution, firstly, glucoamylase is selectively adsorbed to the cross-linked polyglucan containing branched chains having a mean polymerization degree of 2 to 6, preferably 2 to less than 4, or to the cross-linked homooligomer obtained from homooligomer having a polymerization degree of 2 to 6, preferably 2 to less than 4, as an adsorbent. Then the remaining solution containing non-adsorbed components is brought into contact with the cross-linked homooligomer containing branched chains having a mean polymerization degree of 4 to 50, preferably 4 to 20, or with the cross-linked homooligomer obtained from homooligomer having a mean polymerization degree of 4 to 50, preferably 4 to 20, as an adsorbent, thereby to adsorb β-amylase to the adsorbent. The solution finally remained is isolated as an α-amylase-containing solution; alternatively, the solution can also be further contacted with starch by the conventionally known starch adsorption method to adsorb α-amylase and isolate the same from the solution. The adsorbed enzymes are desorbed, for example, from each column with a weakly alkaline aqueous solution or the like, whereby three kinds of the enzymes can be isolated and purified, respectively.

Alternatively, using a crude enzyme solution containing α-amylase, β-amylase and glucoamylase as a sample solution, firstly, glucoamylase and β-amylase are selectively adsorbed to the cross-linked polyglucan containing branched chains having a mean polymerization degree of 4 to 50, preferably 4 to 20, or to the cross-linked homooligomer obtained from homooligomer having a mean polymerization degree of 4 to 50, preferably 4 to 20, as an adsorbent. The thus obtained system containing glucoamylase and β-amylase is subjected to selective adsorption using the adsorbent described above that selectively adsorbs glucoamylase, whereby glucoamylase and β-amylase can be separated from each other.

Further alternatively, a sample solution containing glucoamylase and other amylases is treated with the adsorbent described above that selectively adsorbs glucoamylase, whereby glucoamylase can be selectively isolated from the sample solution.

Still further alternatively, a sample solution containing glucoamylase, β-amylase and other amylases is treated with the adsorbent described above that selectively adsorbs glucoamylase and β-amylase, whereby glucoamylase and β-amylase can be selectively isolated from the sample solution.

The contact of the adsorbent with the crude enzyme solution can be made by methods and devices using any mode of forming a batch mixing bed, a fluidized bed and a packed layer.

The enzymes which are contemplated in the present invention include glucoamylase and β-amylase and, are not particularly limited to their origins as far as they are classified within these enzymes.

Even β-amylases derived from, for example, molds belonging to the genus Aspergillus, the genus Rhizopus or the like, yeasts belonging to the genus Saccharomyces, bacteria belonging to the genus Bacillus and the like are also applicable. Further glucoamylases derived from molds belonging to the genus Aspergillus, the genus Rhizopus or the like, yeasts belonging to the genus Saccharomyces, bacteria belonging to the genus Bacillus, the genus Clostridium and the like are also applicable.

As polyglucans (α-glucans) which are raw materials for producing the adsorbents of the present invention, highly branched glucans are employed. As the degree of branching, those having glucose residues corresponding to the branching points being at least 5% of the total number of the glucose residues in the molecule can be preferably used. More preferably, the degree of branching is 5 to 35%. α-Glucans containing 15% or more of the branching points are much more preferred. Accordingly, examples of naturally occurring α-glucans include glycogen and highly branched amylopectin. These glycogen and highly branched amylopectin are not limited particularly to their origins. For example, even such glycogens that are derived from animals or microorganisms can be used.

As these α-glucans, not only α-glucans isolated from the aforesaid naturally occurring raw materials but processed α-glucans with branched chains shortened by enzyme treatment may also be used. For the treatment of shortening the chain of α-glucans, glucoamylase, β-amylase or α-amylase are preferably used. These enzymes are not limited to particular those kind. The reaction conditions in the treatment can be appropriately chosen depending upon those kind concentration, etc. of α-glucan as substrate but suitably controlled so as to retain the glucose polymerization number in the branched chains of 2 to 6.

When the branching degree of α-glucans is less than 5%, the adsorption capacity of glucoamylase or α-amylase decreases, which is not practical.

As the homooligomers (oligosaccharides) which are raw materials for producing the cross-linked homooligomers used as the adsorbents of the present invention, oligosaccharides having a polymerization number of 2 to 50 in which glucose molecules are linearly polymerized through α-1,4-linkage. These oligosaccharides may be composed of a single component or may be a mixture. In the case of relatively selectively adsorbing either glucoamylase or glucoamylase and β-amylase, however, oligosaccharides having different polymerization degrees are appropriately chosen. Examples of these oligosaccharides include maltose, malto-triose, malto-tetraose, malto-hexose, etc.

For the method of cross-linking of aforesaid homooligomer (oligosaccharides) or polyglucans (α-glucans), there is no particular restriction but, the cross-linking may be performed intermolecularly and/or intramolecularly in such a manner that the solubility of the adsorbent in accordance with the present invention is 0.01 g (i.e., 0.01%) or less, in 100 g of water at temperatures between a freezing point and 60° C., preferably at 60° C., that are used upon adsorption of β-amylase or glucoamylase.

Accordingly, the adsorbent of the present invention prepared by the cross-linking treatment is a hydrated gel or solid. In the hydrated gel formed after immersing the adsorbent obtained by the cross-linking treatment in water at 60° C. for a day, it is preferred that a weight ratio of the hydrated gel be in a range of 3 to 50, based on the adsorbent.

The cross-linking reaction and conditions thereof are appropriately selected depending upon kind or concentration of α-glucans or oligosaccharides, and conditions for use upon adsorption of the enzyme. As an example of the reaction, mention may be made of cross-linking between OH groups in the glucose residues in the presence of epihalogens such as epichlorohydrin, etc. As the epihalogens, epichlorohydrin is most practical. In the case of epihalogens, it is appropriate that the addition amount be 0.5 to 3 times the raw solution of α-glucan or oligosaccharide. It is preferred that the concentration of α-glucan or oligosaccharide in the raw solution be 1% or more. The cross-linking reaction is carried out in the presence of an alkali. As the alkali, a strong alkali such as sodium hydroxide, potassium hydroxide or the like is preferably used; it is preferred that an equimolar amount or more of the alkali be contained, based on the halogen of epihalogens having a concentration of 1N or more. The reaction is conducted at temperatures above 30° C. A reaction time can appropriately be chosen depending upon temperature and concentration of alkali but requires for 30 minutes or longer in the reaction at 60° C. Stirring is effective for contact of the epihalogen phase with the aqueous phase and because of an increase in viscosity of the solution accompanied by formation of the gel.

A pH condition upon the adsorption and desorption of amylases to and from the adsorbent can be appropriately chosen depending upon the objective enzyme, composition of impurities in the crude enzyme solution and properties and purpose of the adsorbent but the adsorption and desorption can be generally practiced under the following conditions.

Upon the adsorption, pH is in a range of 3.0 to 7.5. It is preferred that the pH of a desorbent solution be 7.6 or more but in view of stability of the enzyme, it is generally preferred that the pH be 9.0 or lower as weakly alkaline. Further kind of salts in salt solution used for the desorption is not particularly limited. The salts that are suitably chosen from neutral salts, weakly acidic salts and weakly basic salts are provided for use. Most readily used salt are sodium chloride and potassium chloride.

The salt solution used for the desorption may also be used in combination with the weakly alkaline solution. The salt concentration in the salt solution varies depending upon properties of enzyme to be isolated and purified, kind of salt, pH of solution, etc. but the salt solution is generally operated at 0.5M or more. The salt solution of 3M or more is not practical because subsequent desalting operation, inactivation or salting out of enzyme tend to be caused and therefore, not practical.

Next, embodiments of the method and device for isolation and purification according to the present invention will be described by referring to flow charts shown in FIGS. 4 through 6.

Figure 4:
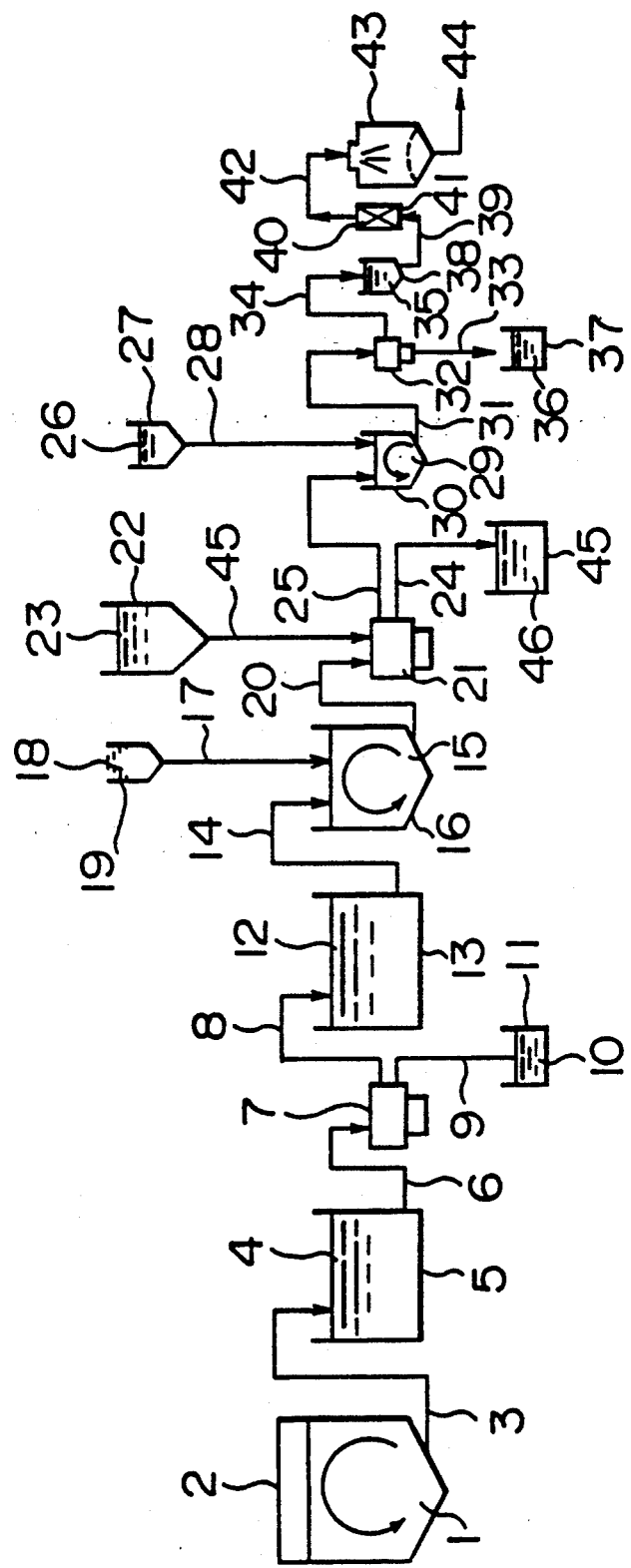
FIG. 4 shows a device used for isolation and purification of glucoamylase or β-amylase which is used for contacting an adsorbent with a cell-free culture solution by suspension-mixing.

In a device shown in FIG. 4, enzyme-producing bacteria capable of producing one or both of glucoamylase and β-amylase are cultured in culture tank 2 to give culture solution 1. Conditions for the culture are appropriately chosen depending upon properties of bacteria and purpose of producing enzyme. After completion of the culture, culture solution 1 is stored in storage tank 4 via transfer pipe 3. Then, the culture solution is separated into cell slurry 10 and cell-free culture solution 12 by a solid-liquid separation device such as centrifugal separation, etc. The cell-free culture solution 12 containing amylases is stored in storage tank 13 further via transfer pipe 8. The cell-free culture solution 12 is introduced into amylase adsorption tank 16. Adsorbent 18 of the present invention which selectively adsorbs the amylase to be isolated out of the amylases is charged from storage tank 19 into adsorption tank 16 via pipe 17, whereby mixing is performed under definite conditions to contact the solid with the liquid. The properties of liquid upon the contact, for example, pH, temperature and salt concentration, are suitably selected so as to give the aforesaid ranges, depending upon kind of amylase to be adsorbed. In the case shown in this figure, the contact is made under stirring, for example, by mechanical stirring using a stirring imppeller. The contact is made in a low tank temperature range in which enzymatic hydrolysis of the α-1,4-linkage and β-1,6-linkage of glucose does not substantially occur. A time period required for the adsorption is also suitably chosen, as described above. After completion of the adsorption, mixture 15 of the adsorbent for amylase and cell-free culture solution is introduced into solid-liquid separation device 21. Here the amylase-adsorbed adsorbent is isolated from the solution and then the adhered solution is rinsed and removed with rising water 22. The thus obtained amylase-adsorbed and rinsing-treated adsorbent 25 is transferred to desorption tank 30. On the other hand, amylase-free culture solution and rinsing waste 46 are stored in storage tank 45 via pipe 24. The amylase-adsorbed and rinsing-treated adsorbent is brought into contact with desorbent solution 26, whereby the adsorbed amylase is desorbed. The desorbed adsorbent-desorbing solution mixture 29 is again subjected to solid-liquid separation in solid-liquid separation device 32. The adsorbent 36 from which the isolated amylase has been desorbed is separated from amylase desorbed solution 35. The amylase-desorbed solution is stored in storage tank 38 and, if necessary and desired, introduced in desalting device 40 to remove salts and alkali components in the desorbent solution. The amylase-containing solution treated for desalting is suitably isolated by concentration-drying device 43 as the concentrate or dry powders.

In the FIG. 4, numeral 5 indicates a storage tank for culture solution; 6 indicates a transfer pipe for culture solution; 7 indicates a solid-liquid separation device; 9 indicates a transfer pipe for cell slurry; 11 indicates a cell slurry storage tank; 14 indicates a transfer pipe for cell-free culture solution; 20 indicates a transfer pipe for a mixture of adsorbent for amylase and cell-free culture solution 1; 23 indicates rinsing water; 27 indicates a storage tank for adsorbent solution; 28 indicates a transfer pipe for desorbent solution; 31 indicates a transfer pipe for an adsorbentdesorbent solution mixture; 33 indicates a transfer pipe for adsorbent from which amylase has been desorbed; 34 indicates a transfer pipe for amylase-desorbed solution; 37 indicates a storage tank for adsorbent from which amylase has been desorbed; 39 indicates a transfer pipe for amylase-desorbed solution; 41 indicates an ion exchanger for desalting; 42 indicates a desalting-treated amylase solution; and 44 indicates concentrated and dried amylase.

Figure 5:
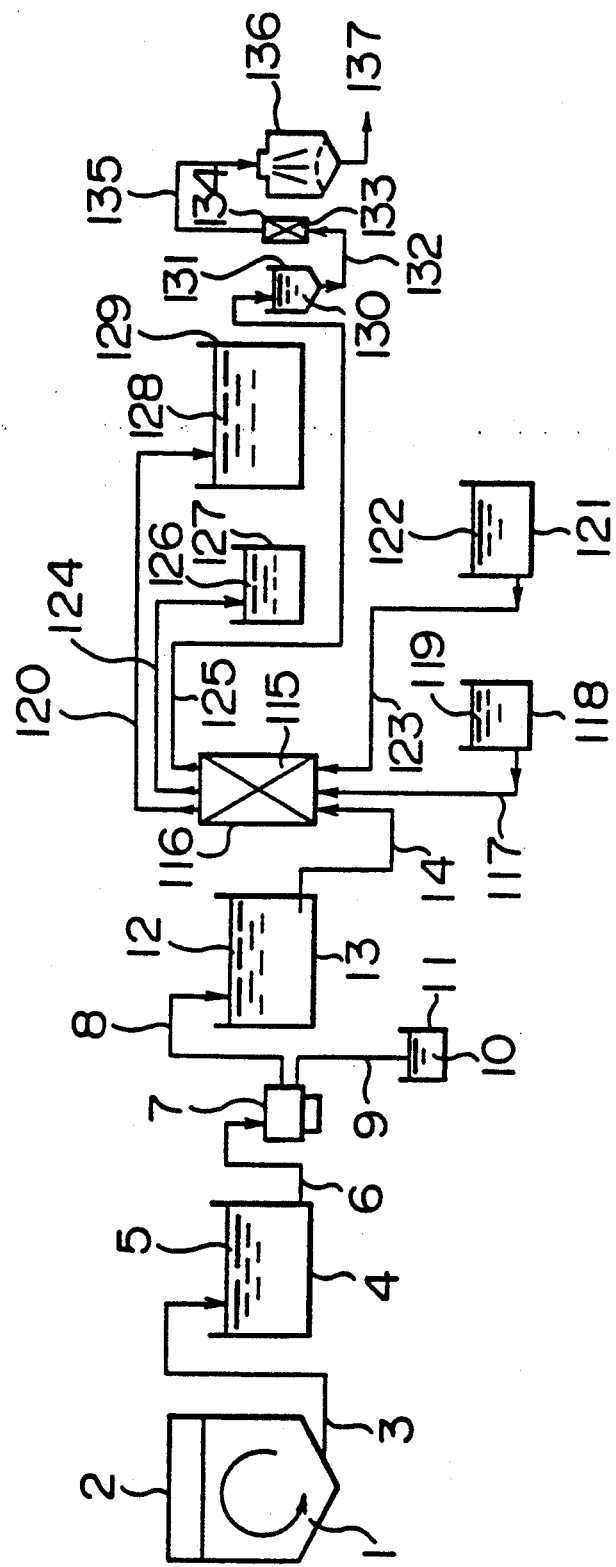
FIG. 5 shows a device for isolation and purification of amylases in which contact of an adsorbent with a cell-free culture solution is performed using a packed column.

Alternatively, as shown in the flow chart of FIG. 5, the contact of the adsorbent with the cell-free culture solution can also be performed by a packed column packed with adsorbent 115, instead of the suspension-mixing as shown in FIG. 4. Firstly, the cell-free culture solution 112 is moved to amylase adsorption tower 116 via transfer pipe 114, where the amylase is adsorbed to adsorbent 115 packed in the tower. Then, rinsing water 119 is passed through adsorption tower 116 through pipe 117 to rinse. Rinsing waste 126 is stored in storage tank 127. Next, desorbent solution 122 is introduced into adsorption tower 116 via pipe 123, where the amylase is desorbed. The amylase-desorbed solution 130 containing amylase is, if necessary and desired, desalted, concentrated and dried, as in FIG. 4.

In the FIG. 5, numeral 118 indicates a storage tank for rinsing water; 120 indicates a transfer pipe for amylase-free culture solution; 121 indicates a storage tank for desorbent solution; 124 indicates a transfer pipe for rinsing waste; 125 indicates a transfer pipe for amylase-desorbed solution; 128 indicates an amylase-free culture solution; 129 indicates a storage tank for amylase-free culture solution; 131 indicates a storage tank for amylase-desorbed solution; 132 indicates a transfer pipe for amylase-desorbed solution; 133 indicates an ion exchanger for desalting; 134 indicates a desalting device; 135 indicates a transfer pipe for desalting-treated amylase solution; 136 indicates a concentration-drying device; and 137 indicates concentrated and dried amylase.

Figure 6:
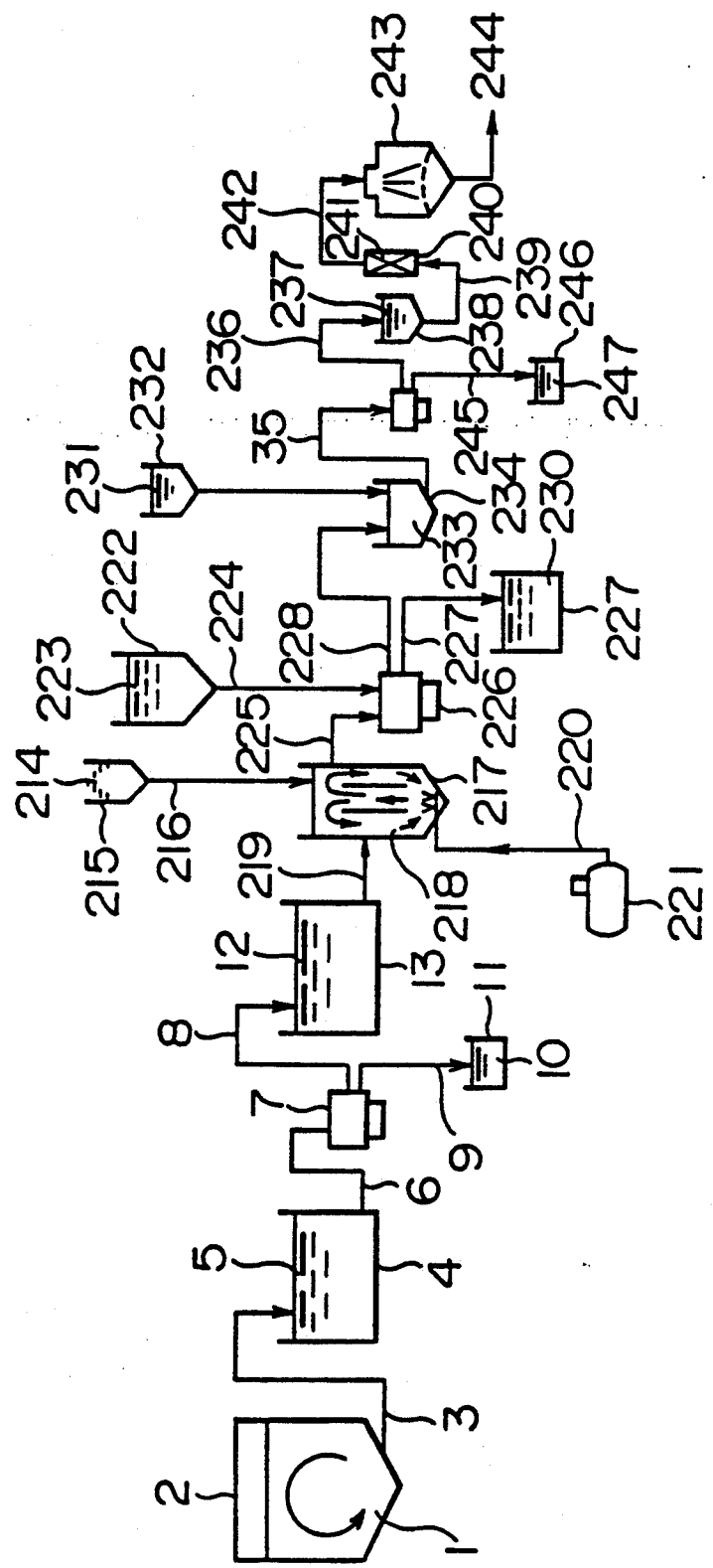
FIG. 6 shows a device for isolation and purification of amylases in which contact of an adsorbent with a cell-free culture solution is performed using a fluidized bed.

FIG. 6 shows a modification of the suspension mixing shown in FIG. 4, wherein adsorption is carried out in a fluidized bed. Cell-free culture solution 12 is introduced in fluidized bed type amylase adsorption tank 217, where the solution is brought into contact with adsorbent 214 while fluidizing the culture solution by compressed air supplied from air compressor 221. The flow after the contact is as in FIG. 4.

In the FIG. 6, numeral 215 is a storage tank of adsorbent for amylase; 216 indicates a transfer pipe of adsorbent for amylase; 218 indicates an adsorbent for amylase and cell-free culture solution mixture; 219 indicates a transfer pipe for cell-free culture solution; 220 indicates a transfer pipe for air; 222 indicates a storage tank for rinsing water; 223 indicates rinsing water; 224 indicates a transfer pipe for rinsing water; 225 indicates a transfer pipe of adsorbent for amylase and cell-free culture solution mixture; 226 indicates a solid-liquid separation device; 227 indicates a transfer pipe for amylase-free culture solution and rinsing waste; 228 indicates a transfer pipe for amylase-adsorbed and rinsing-treated culture solution; 229 indicates a storage tank for amylase-free culture solution and rinsing waste; 230 indicates an amylase-free culture solution and rinsing water; 231 indicates an adsorbent solution; 232 indicates a storage tank for desorbent solution; 233 indicates an adsorbent and desorbent solution mixture; 234 indicates a desorption tank; 235 indicates a transfer pipe for adsorbent and desorbent solution mixture; 236 indicates a transfer pipe for amylase-desorbed solution; 237 indicates an amylase-desorbed solution; 238 indicates a storage tank for amylase-desorbed solution; 239 indicates a transfer pipe for amylase-desorbed solution; 240 indicates a desalting device; 241 indicates an ion exchanger for desalting; 242 indicates a transfer pipe for desalting-treated amylase solution; 243 indicates a concentration drying device; and 244 indicates concentrated and dried amylase.

According to the method for isolation and purification of amylases and the device for the same of the present invention, there are used as adsorbents the cross-linked polyglucans capable of controlling the length of the branched chains thereof or cross-linked homooligomers capable of controlling the length of main chain, namely, the adsorbents in which the length of branched chain or main chain of the adsorbents can be controlled, in response to the amylase to be isolated and purified and which become insoluble in water by the three-dimensional cross-linking inter-molecularly and/or intramolecularly. For this reason, the objective amylase can easily be concentrated and purified from solutions such as crude enzyme solutions or the like, containing many and various organic and inorganic impurities and other enzymes, simply by adsorbing and desorbing the amylase. Therefore, according to the present invention the process for purification of amylases can be greatly simplified.

Hereafter the present invention will be described in more detail by referring to the examples of the present invention.

EXAMPLE 1

Isolation and Purification of β-Amylase and Glucoamylase Using Cross-linked Glycogen To 10 g of dry powders of glycogen (estimated molecular weight, $4 \times 10^5$; estimated branching degree, 25%) prepared from Escherichia coli cells was added 90 ml of water. The mixture was heated to 70° C. with stirring to dissolve the powders and make a viscous solution. To the solution was added 33 ml of 6N sodium hydroxide. The mixture was charged in a 500 ml reaction flask equipped with a stirrer and a reflux condenser. Then, 140 ml of epichlorohydrin was added to the mixture followed by heating at 50° C. for 5 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered. The recovered gel was again suspended in 50 ml of ethanol. The suspension was filtered to recover the gelatinous product. This operation was repeated further 3 times. Next, the gelatinous product was suspended in 50 ml of distilled water and isolated by filtration. After repeating this operation 3 times, the matter was again dispersed in 50 ml of ethanol. The dispersion was filtered. After drying, the gelatinous product was ground into powders to give 9.2 g of white powders.

The solubility of the powders in water at 60° C. was 0.002 g or less, based on 100 g of water. After further immersing the powders in water of 60° C. for a day, a weight ratio of the hydrated gel to the powders was 11.5.

On the other hand, 40 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. They were contacted with each other by mixing for 2 minutes at 5 rpm. The mixture was filtered and, α-amylase activity, β-amylase activity and glucoamylase activity in the filtrate were measured.

In the supernatant, α-amylase, β-amylase and glucoamylase were 0.50 units/ml, 0.02 units/ml and 0.01 unit/ml, respectively.

The amount of each enzyme adsorbed to the adsorbent described above was calculated as a value obtained by subtracting an enzyme concentration after the contact with the adsorbent from an enzyme concentration prior to the contact. As a result, α-amylase present in the culture filtrate was not substantially adsorbed but 98% (38.4 units) of β-amylase and 99% (51.6 units) of glucoamylase were adsorbed to the adsorbent.

Next, the adsorbent to which the aforesaid enzymes had been adsorbed was put in a container of 20 ml and 4 ml of a solution adjusted to pH 8 with sodium hydroxide was added to the adsorbent. The mixture was stirred at 5 rpm for 2 minutes to contact them with each other. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into the rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, no α-amylase was detected but β-amylase and glucoamylase were 6.40 units/ml and 8.60 units/ml, respectively. By multiplying the concentrations of respective enzymes in the desorbed solution by 6 ml of the amount of solution, respective recovery amounts were determined to be 0 unit of α-amylase, 38.4 units of β-amylase and 51.6 units of glucoamylase. Thus, the enzymes present in the raw solution could be recovered in 0% of α-amylase, 98% of β-amylase and 99% of glucoamylase, by the adsorption and desorption of this example. Further in the solution, any protease activity was not detected and neither coloration nor odor was noted. Furthermore, amounts of organic and inorganic materials in the solution were reduced to 1.1% and 1.0%, respectively, based on the contents in the raw solution.

From the foregoing, β-amylase and glucoamylase in the raw solution could be concentrated to about 5 times and purified.

EXAMPLE 2

Isolation and Purification of β-Amylase and Glucoamylase Using Cross-linked Glycogen The cross-linked glycogen prepared in Example 1 was taken by 5 g, which was packed in a column of 10 $\phi \times 70$ mm.

Through the column was passed 80 ml of a culture filtrate of Aspergillus oryzae IFO-4176 having the same lot as used in Example 1 at a temperature of 6° C. in a flow rate of 3 ml/min. The column filtrates were collected and enzyme concentrations in the solution were measured.

As a result, α-amylase, β-amylase and glucoamylase were 0.5 units/ml, 0.03 units/ml and 0.01 unit/ml, respectively.

The amount of each enzyme adsorbed to the adsorbent described above was calculated as a value obtained by subtracting an enzyme concentration after the contact with the adsorbent from an enzyme concentration prior to the contact. As a result, α-amylase, β-amylase and glucoamylase were adsorbed by 0 unit, 76 units and 103.2 units, respectively. Accordingly, α-amylase present in the culture filtrate was not adsorbed but 97% of α-amylase and 99% of glucoamylase were adsorbed to the adsorbent.

Next, 4 ml of water was passed through the column described above to wash it. Through the washed column was passed 15 ml of a solution adjusted to pH 8.0 with sodium hydroxide, at 6° C. in a flow rate of 0.5 ml/min. Then, 5 ml of water was passed therethrough and the rinsing solution was recovered. The effluent and rinsing solution described above were combined to give 20 ml of the enzyme-desorbed solution.

The enzyme concentrations in the enzyme-desorbed solution were measured. As a result, no α-amylase was detected but β-amylase and glucoamylase were 12.5 units/ml and 16.9 units/ml, respectively. By multiplying the concentrations of respective enzymes in the desorbed solution by 20 ml of the amount of solution, respective recovery amounts were determined. Thus, α-amylase, β-amylase and glucoamylase were 0 unit, 76 units and 10 units, respectively. Namely, among the enzymes present in the raw solution, 0% of α-amylase, 97% of β-amylase and 96% of glucoamylase could be recovered.

Further in the solution, any protease activity was not detected and neither coloration nor odor was noted. Furthermore, amounts of organic and inorganic materials in the solution were reduced to 1.1% and 1.0%, respectively, based on the contents in the raw solution.

From the foregoing, β-amylase and glucoamylase in the raw solution could be concentrated to about 4 times and purified.

EXAMPLE 3

Isolation and Purification of β-Amylase and Glucoamylase Using Cross-linked Glycogen To 10 g of dry powders of glycogen (estimated molecular weight, $4 \times 10^5$; estimated branching degree, 27%) of bovine liver was added 90 ml of water. The mixture was heated to 70° C. with stirring to dissolve the powders and make a viscous solution. To the solution was added 33 ml of 4N sodium hydroxide. The mixture was charged in a 500 ml reaction flask equipped with a stirrer and a reflux condenser. Then, 140 ml of epichlorohydrin was added to the mixture followed by heating at 50° C. for 5 hours with stirring at 20 rpm.

After completion of the reaction, the content was cooled to room temperature and the gelatinous product in the lower aqueous phase was filtered. To the gelatinous product was added 50 ml of ethanol. After stirring the gelatinous product was filtered and recovered. The recovered gel was again suspended in 50 ml of ethanol. The suspension was filtered to recover the gelatinous product. This operation was repeated further 3 times. Next, the gelatinous product was suspended in 50 ml of distilled water and isolated by filtration. After repeating this operation 3 times, the matter was again dispersed in 50 ml of ethanol. The dispersion was filtered. After drying, the gelatinous product was ground into powders to give 9.3 g of white powders.

The solubility of the powders in water at 60° C. was 0.003 g or less, based on 100 g of water. After further immersing the powders in water of 60° C. for a day, a weight ratio of the hydrated gel to the powders was 12.3.

Next, the following experiment was performed to see adsorption property of glucoamylase to the powders.

Forty milliliters of a culture filtrate (containing 0.50 units/ml of $\alpha$-amylase, 0.98 units/ml of $\beta$-amylase and 1.30 units/ml of glucoamylase) of Aspergillus oryzae IFO-4176 was cooled to 6° C. and 0.2 g of the adsorbent powders described above was added thereto. They were contacted with each other by mixing for 2 minutes at 5 rpm. The mixture was filtered through a column (10 $\phi \times 50$ mm) equipped with a filter at the bottom thereof and, $\alpha$-amylase activity, $\beta$-amylase activity and glucoamylase activity in the filtrate were measured.

In the supernatant, $\alpha$-amylase, $\beta$-amylase and glucoamylase were 0.50 units/ml, 0.03 units/ml and 0.02 units/ml, respectively.

The amount of each enzyme adsorbed to the adsorbent described above was calculated as a value obtained by subtracting an enzyme concentration after the contact with the adsorbent from an enzyme concentration prior to the contact. As a result, $\alpha$-amylase present in the culture filtrate was not substantially adsorbed but 97% (0.95 units) of $\beta$-amylase and 98% (1.28 units) of glucoamylase were adsorbed to the adsorbent.

Next, 0.5M sodium chloride aqueous solution (pH 7.0) was flown through the column to which the aforesaid enzymes had been adsorbed and the effluent was recovered. Thereafter, 2 ml of water was flown to rinse the column. The rinsing liquid and the effluent described above were combined to give 6 ml of the enzyme-desorbed solution.

The enzyme concentrations in the enzyme-desorbed solution described above were measured. As a result, no $\beta$-amylase was detected but $\alpha$-amylase and glucoamylase were 6.2 units/ml and 8.6 units/ml, respectively. By multiplying the concentrations of respective enzymes in the desorbed solution by 6 ml of the amount of solution, respective recovery amounts were determined to be 0 unit of $\alpha$-amylase, 37.2 units of $\beta$-amylase and 51.2 units of glucoamylase. Thus, among the enzymes present in the raw solution, 0% of $\alpha$-amylase, 95% of $\beta$-amylase and 96% of glucoamylase could be recovered, by the adsorption and desorption of this example. Further in the solution, any protease activity was not detected and neither coloration nor odor was noted. Furthermore, amounts of organic and inorganic materials in the solution were reduced to 1.1% and 1.0%, respectively, based on the contents in the raw solution.

From the foregoing, $\beta$-amylase and glucoamylase in the raw solution could be concentrated to about 5 times and purified.

EXAMPLE 4

Isolation and Purification of $\beta$-Amylase and Glucoamylase Using Cross-linked Glycogen To 10 g of dry powders of glycogen (estimated molecular weight, $4 \times 10^5$, estimated branching degree, 25%) prepared from oyster was added 90 ml of water. The mixture was heated to 70° C. with stirring to dissolve the powders and make a viscous solution.

To the solution was added 33 ml of 6N sodium hydroxide. The mixture was charged in a 500 ml reaction flask equipped with a stirrer and a reflux condenser. Then, 140 ml of epichlorohydrin was added to the mixture followed by heating at 50° C. for 5 hours with stirring at 15 rpm.

After completion of the reaction, the content was cooled to room temperature and the gelled product in the lower aqueous phase was filtered. To the gelatinous product was added 50 ml of ethanol. After stirring the gelatinous product was filtered and recovered. The recovered gel was again suspended in 50 ml of ethanol. The suspension was filtered to recover the gelatinous product.

This operation was repeated further 3 times. Next, the gelatinous product was suspended in 50 ml of distilled water and isolated by filtration. This operation was repeated further 3 times. Next, the matter was again dispersed in distilled water followed by filtration. After repeating this operation 3 times, the matter was again dispersed in 50 ml of ethanol.

The dispersion was filtered. After drying, the gelatinous product was ground into powders to give 9.1 g of white powders.

The solubility of the powders in water at 60° C. was 0.001 g or less, based on 100 g of water. After further immersing the powders in water of 60° C. for a day, a weight ratio of the hydrated gel to the powders was 10.8.

Next, the following experiment was performed to see adsorption property of glucoamylase to the powders.

Forty milliliters of a culture filtrate (containing 0.50 units/ml of $\alpha$-amylase, 0.98 units/ml of $\beta$-amylase and 1.30 units/ml of glucoamylase) of Aspergillus oryzae IFO-4176 was cooled to 6° C. and charged in a fluidized phase type adsorption tank. The tank had a structure comprising an outer cylinder ($\phi 28$ mm $\times 100$ mm) having a draft tube ($\phi$ 15 mm $\times 70$ mm) therein in which an air blow single pore nozzle (inner diameter of 1 mm) for fluidizing the solution. Then, 0.2 g of the adsorbent powders described above was added thereto and air was injected at a vacant tower rate of 0.5 cm/sec thereby to fluidize and contact the solution in the tank with the powders for 2 minutes. The solution was filtered through a column (10 $\phi \times 50$ mm) equipped with a filter at the bottom thereof and, $\alpha$-amylase activity, $\beta$-amylase activity and glucoamylase activity in the filtrate were measured.

In the supernatant, $\alpha$-amylase, $\beta$-amylase and glucoamylase were 0.50 units/ml, 0.04 units/ml and 0.03 units/ml, respectively. The amount of each enzyme adsorbed to the adsorbent described above was calculated as a value obtained by subtracting an enzyme concentration after the contact with the adsorbent from an enzyme concentration prior to the contact. As a result, α-amylase present in the culture filtrate was not substantially adsorbed but 96% (0.94 units/ml) of β-amylase and 98% (1.27 units/ml) of glucoamylase were adsorbed to the adsorbent.

Next, 0.5M sodium chloride aqueous solution (pH 7.0) was flown through the column to which the aforesaid enzymes had been adsorbed and the effluent was recovered. Thereafter, 2 ml of water was flown to rinse the column. The rinsing liquid and the effluent described above were combined to give 6 ml of the enzyme-desorbed solution.

The enzyme concentrations in the enzyme-desorbed solution described above were measured. As a result, no α-amylase was detected but β-amylase and glucoamylase were 6.2 units/ml and 8.4 units/ml, respectively. By multiplying the concentrations of respective enzymes in the desorbed solution by 6 ml of the amount of solution, respective recovery amounts were determined to be 0 unit of α-amylase, 37.4 units of β-amylase and 50.1 units of glucoamylase. Thus, among the enzymes present in the 0% of α-amylase, 95% of β-amylase and 96% of glucoamylase could be recovered by the adsorption and desorption of this example. Further in the solution, any protease activity was not detected and neither coloration nor odor was noted. Furthermore, amounts of organic and inorganic matters in the solution were reduced to 1.2% and 1.1%, respectively, based on the contents in the raw solution.

From the foregoing, β-amylase and glucoamylase in the raw solution could be concentrated to about 5 times and purified.

EXAMPLE 5

Isolation and Purification of β-Amylase and Glucoamylase Using Cross-linked Glycogen Treated With Glucoamylase To 10 g of dry powders of glycogen (estimated molecular weight, $4 \times 10^5$; estimated branching degree, 25%) of Escherichia coli was added 95 ml of 0.05M sodium acetate buffer (pH 5.0). The mixture was heated to 70° C. with stirring to dissolve the powders. The solution was cooled to 50° C. Thirty milliliters of the solution was taken and, 2 ml of a glucoamylase solution in which 10 units of glucoamylase derived from Aspergillus oryzae IFO-4176 were dissolved, was added thereto. The mixture was kept at 40° C.

The amount of glucose produced 2 hours later was measured and as a result, reached approximately 30% based on the number of the glucose residues in the weight was $6 \times 10^4$.

The solution was packed in a cellophane tube for dialysis and dialyzed to 5 l of water at 10° C. for 10 hours. The content was freeze dried to give 0.9 g of white powders.

To the powders was added 10 ml of water. The mixture was heated to 70° C. with stirring to dissolve the powders and make a viscous solution. To the solution was added 33 ml of 6N sodium hydroxide. The mixture was charged in a 200 ml reaction flask equipped with a stirrer and a reflux condenser. Then, 100 ml of epichlorohydrin was added to the mixture followed by heating at 70° C. for 5 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered. The recovered gel was again suspended in 50 ml of ethanol. The suspension was filtered to recover the gelatinous product. This operation was repeated further 3 times. Next, the gelatinous product was suspended in 50 ml of distilled water and isolated by filtration. After repeating this operation 3 times, the matter was again dispersed in 50 ml of ethanol. The dispersion was filtered. After drying, the gelatinous product was ground into powders to give 0.7 g of white powders.

The solubility of the powders in water at 60° C. was 0.001 g or less, based on 100 g of water. After further immersing the powders in water of 60° C. for a day, a weight ratio of the hydrated gel to the powders was 13.2. By measurement of the non-reducing terminal glucose residue of the powders, a mean polymerization degree of the branched chains was determined to be 4.2.

Next, the following experiment was performed to see adsorption property of glucoamylase to the powders.

Forty milliliters of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. They were contacted with each other by mixing for 2 minutes at 5 rpm. The content was filtered through a column (10 $\phi \times 50$ mm) equipped with a filter at the bottom thereof and, α-amylase activity, β-amylase activity and glucoamylase activity in the filtrate were measured.

In the supernatant, α-amylase, β-amylase and glucoamylase were 0.50 units/ml, 0.50 units/ml and 0.01 unit/ml, respectively. The amount of each enzyme adsorbed to the adsorbent described above was calculated as a value obtained by subtracting an enzyme concentration after the contact with the adsorbent from an enzyme concentration prior to the contact. As a result, α-amylase present in the culture filtrate was not substantially adsorbed but 51% (0.48 units/ml) of β-amylase and 99% (1.29 units/ml) of glucoamylase were adsorbed to the adsorbent.

Next, 0.5M sodium chloride aqueous solution (pH 7.0), which had been adjusted with a sodium hydroxide solution to pH 7.5, was flown through the column to which the aforesaid enzymes had been adsorbed and the effluent was recovered. Thereafter, 2 ml of water was flown to rinse the column. The rinsing liquid and the effluent described above were combined to give 6 ml of the enzyme-desorbed solution.

The enzyme concentrations in the enzyme-desorbed solution described above were measured. As a result, no α-amylase was detected but β-amylase and glucoamylase were 3.1 units/ml and 8.5 units/ml, respectively. By multiplying the concentrations of respective enzymes in the desorbed solution by 6 ml of the amount of solution, respective recovery amounts were determined to be 0 unit of α-amylase, 20 units of β-amylase and 51.0 units of glucoamylase. Thus, among the enzymes present in the raw solution, 0% of α-amylase, 51.0% of β-amylase and 98% of glucoamylase could be recovered, by the adsorption and desorption of this example. Further in the solution, any protease activity was not detected and neither coloration nor odor was noted. Furthermore, amounts of organic and inorganic materials in the solution were reduced to 0.9% and 1.1%, respectively, based on the contents in the raw solution.

From the foregoing, β-amylase and glucoamylase in the raw solution could be concentrated to about 3.4 times and about 5 times, respectively, and purified.

EXAMPLE 6

Isolation and Purification of Glucoamylase Using Cross-linked Maltose

To 10 g of dry powders of maltose was added 90 ml of water. The mixture was heated to 50° C. with stirring to dissolve the powders. To the solution was added 33 ml of 3N sodium hydroxide. The mixture was charged in a 500 ml reaction flask equipped with a stirrer and a reflux condenser. Then, 140 ml of epichlorohydrin was added to the mixture followed by heating at 70° C. for 15 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered. The recovered gel was again suspended in 50 ml of ethanol. The suspension was filtered to recover the gelatinous product. This operation was repeated further 3 times. Next, the gelatinous product was suspended in 50 ml of distilled water and isolated by filtration. After repeating this operation 3 times, the matter was again dispersed in 50 ml of ethanol. The dispersion was filtered. After drying, the gelatinous product was ground into powders to give 9.4 g of white powders.

The solubility of the powders in water at 60° C. was 0.002 g or less, based on 100 g of water. After further immersing the powders in water of 60° C. for a day, a weight ratio of the hydrated gel to the powders was 14.0.

On the other hand, 20 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. The mixture was stirred at 5 rpm for 2 minutes. The mixture was filtered to give 20 ml of the filtrate. α-Amylase activity, β-amylase activity and glucoamylase activity in the filtrate were measured.

In the supernatant, α-amylase, β-amylase and glucoamylase were 0.50 units/ml, 0.97 units/ml and 0.01 unit/ml, respectively.

The amount of each enzyme adsorbed to the adsorbent described above was calculated as a value obtained by subtracting an enzyme concentration after the contact with the adsorbent from an enzyme concentration prior to the contact. As a result, α-amylase, β-amylase and glucoamylase were adsorbed to the adsorbent by 0 unit/ml, 0.015 units/ml and 1.29 units/ml, of the culture filtrate, respectively. Accordingly, 0% of α-amylase, 1% of β-amylase and 99% of glucoamylase were adsorbed to the adsorbent.

Next, the adsorbent to which the aforesaid enzymes had been adsorbed was put in a container of 20 ml and 4 ml of a solution adjusted to pH 8 with sodium hydroxide was added to the adsorbent. The mixture was stirred at 5 rpm for 2 minutes to contact them. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into the rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, α-amylase, β-amylase and glucoamylase were 0 units/ml, 0.65 units/ml and 4.25 units/ml, respectively. Thus, 0 unit (recovery rate, 0%) of α-amylase, 3.9 units (2%) of β-amylase and 25.5 units (98%) of glucoamylase could be recovered.

Further in the solution, any protease activity was not detected and neither coloration nor odor was noted. Furthermore, amounts of organic and inorganic materials in the solution were reduced to 1.5% and 1.4%, respectively, based on the contents in the raw solution. From the foregoing, glucoamylase in the raw solution could be selectively concentrated to about 3 times and purified.

EXAMPLE 7

Isolation and Purification of Glucoamylase Using Cross-linked Maltose

To 10 g of dry powders of maltose was added 80 ml of water. The mixture was heated to 50° C. with stirring to dissolve the powders. To the solution was added 33 ml of 4N sodium hydroxide. The mixture was charged in a 500 ml reaction flask equipped with a stirrer and a reflux condenser.

Then, 140 ml of epichlorohydrin was added to the mixture followed by heating at 80° C. for 6 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered.

The recovered gel was again suspended in 50 ml of ethanol. The suspension was filtered to recover the gelatinous product. This operation was repeated further 3 times. Next, the gelatinous product was suspended in 50 ml of distilled water and isolated by filtration.

After repeating this operation 3 times, the matter was again dispersed in 50 ml of ethanol. The dispersion was filtered. After drying, the gelatinous product was ground into powders to give 18.1 g of white powders.

The solubility of the powders in water at 60° C. was 0.003 g or less, based on 100 g of water. After further immersing the powders in water of 60° C. for a day, a weight ratio of the hydrated gel to the powders was 15.2.

On the other hand, 20 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. The mixture was stirred at 5 rpm for 2 minutes. The mixture was filtered and, α-amylase activity, β-amylase activity and glucoamylase activity in the filtrate were measured.

The respective enzyme activities in the supernatant were measured. In the supernatant, α-amylase, β-amylase and glucoamylase were 0.50 units/ml, 0.88 units/ml and 0.01 unit/ml, respectively.

The amount of each enzyme adsorbed to the adsorbent described above was calculated as a value obtained by subtracting an enzyme concentration after the contact with the adsorbent from an enzyme concentration prior to the contact. As a result, α-amylase, β-amylase and glucoamylase were adsorbed to the adsorbent by 0 unit/ml, 0.12 units/ml and 1.29 units/ml, of the culture filtrate, respectively.

Accordingly, α-amylase present in the culture filtrate was not adsorbed at all but, 12.0% of β-amylase and 99% of glucoamylase were adsorbed to the adsorbent.

Next, the adsorbent to which the aforesaid enzymes had been adsorbed was put in a container of 20 ml and 4 ml of a solution adjusted to pH 8 with sodium hydroxide was added to the adsorbent. The mixture was stirred at 5 rpm for 2 minutes to contact them. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into the rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, α-amylase, β-amylase and glucoamylase were 0 units/ml, 0.35 units/ml and 4.14 units/ml, respectively. Thus, 0 unit (recovery rate, 0%) of α-amylase, 2.1 units (10.7%) of β-amylase and 24.8 units (95%) of glucoamylase could be recovered.

Further in the solution, any protease activity was not detected and neither coloration nor odor was noted. Furthermore, amounts of organic and inorganic materials in the solution were reduced to 1.4% and 1.2%, respectively, based on the contents in the raw solution. From the foregoing, glucoamylase in the raw solution could be selectively concentrated to about 3.2 times and purified.

EXAMPLE 8

Isolation and Purification of Glucoamylase Using Cross-linked Maltotriose

To 10 g of dry powders of maltotriose was added 80 ml of water. The mixture was heated to 50° C. with stirring to dissolve the powders. To the solution was added 33 ml of 4N sodium hydroxide. The mixture was charged in a 500 ml reaction flask equipped with a stirrer and a reflux condenser.

Then, 140 ml of epichlorohydrin was added to the mixture followed by heating at 80° C. for 6 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered.

The recovered gel was again suspended in 50 ml of ethanol. The suspension was filtered to recover the gelatinous product. This operation was repeated further 3 times. Next, the gelatinous product was suspended in 50 ml of distilled water and isolated by filtration.

After repeating this operation 3 times, the matter was again dispersed in 50 ml of ethanol. The dispersion was filtered. After drying, the gelatinous product was ground into powders to give 9.7 g of white powders.

The solubility of the powders in water at 60° C. was 0.002 g or less, based on 100 g of water. After further immersing the powders in water of 60° C. for a day, a weight ratio of the hydrated gel to the powders was 14.8.

On the other hand, 20 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. The mixture was stirred at 5 rpm for 2 minutes. The mixture was filtered and, α-amylase activity, β-amylase activity and glucoamylase activity in the filtrate were measured.

The respective enzyme activities in the supernatant were measured. In the supernatant, α-amylase, β-amylase and glucoamylase were 0.50 units/ml, 0.64 units/ml and 0.03 units/ml, respectively.

The amount of each enzyme adsorbed to the adsorbent described above was calculated as a value obtained by subtracting an enzyme concentration after the contact with the adsorbent from an enzyme concentration prior to the contact.

As a result, α-amylase, β-amylase and glucoamylase were adsorbed to the adsorbent by 0 unit/ml, 0.34 units/ml and 1.27 units/ml, of the culture filtrate, respectively.

Accordingly, α-amylase present in the culture filtrate was not adsorbed at all but, 35% of β-amylase and 98% of glucoamylase were adsorbed to the adsorbent.

Next, the adsorbent to which the aforesaid enzymes had been adsorbed was put in a container of 20 ml and 4 ml of a solution adjusted to pH 8.2 with sodium hydroxide was added to the adsorbent. The mixture was stirred at 5 rpm for 2 minutes to contact them. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, α-amylase, β-amylase and glucoamylase were 0 units/ml, 1.05 units/ml and 4.16 units/ml, respectively. Thus, 0 unit (recovery rate, 0%) of α-amylase, 6.27 units (32%) of β-amylase and 25.0 units (96%) of glucoamylase could be recovered.

Further in the solution, any protease activity was not detected and neither coloration nor odor was noted. Furthermore, amounts of organic and inorganic materials in the solution were reduced to 1.7% and 1.2%, respectively, based on the contents in the raw solution. From the foregoing, glucoamylase in the raw solution could be selectively concentrated to about 3.2 times and purified.

EXAMPLE 9

Isolation and Purification of β-Amylase and Glucoamylase Using Cross-linked Maltotetraose To 1 g of dry powders of maltotetraose was added 8 ml of water. The mixture was heated to 50° C. with stirring to dissolve the powders. To the solution was added 33 ml of 4N sodium hydroxide. The mixture was charged in a 200 ml reaction flask equipped with a stirrer and a reflux condenser.

Then, 15 ml of epichlorohydrin was added to the mixture followed by heating at 80° C. for 6 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered.

The recovered gel was again suspended in 50 ml of ethanol. The suspension was filtered to recover the gelatinous product. This operation was repeated further 3 times. Next, the gelatinous product was suspended in 50 ml of distilled water and isolated by filtration.

After repeating this operation 3 times, the matter was again dispersed in 50 ml of ethanol. The dispersion was filtered. After drying, the gelatinous product was ground into powders to give 0.90 g of white powders.

The solubility of the powders in water at 60° C. was 0.001 g or less, based on 100 g of water. After further immersing the powders in water of 60° C. for a day, a weight ratio of the hydrated gel to the powders was 13.4.

On the other hand, 20 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. The mixture was stirred at 5 rpm for 2 minutes.

The mixture was filtered and, α-amylase activity, β-amylase activity and glucoamylase activity in the filtrate were measured.

In the supernatant, α-amylase, β-amylase and glucoamylase were 0.50 units/ml, 0.29 units/ml and 0.03 units/ml, respectively.

The amount of each enzyme adsorbed to the adsorbent described above was calculated as a value obtained by subtracting an enzyme concentration after the contact with the adsorbent from an enzyme concentration prior to the contact.

As a result, α-mylase, β-amylase and glucoamylase were adsorbed to the adsorbent by 0 unit/ml, 0.69 units/ml and 1.27 units/ml, of the culture filtrate, respectively.

Accordingly, α-amylase present in the culture filtrate was not adsorbed at all but, 70% of β-amylase and 98% of glucoamylase were adsorbed to the adsorbent.

Next, the adsorbent to which the aforesaid enzymes had been adsorbed was put in a container of 20 ml and 4 ml of a solution adjusted to pH 8.2 with sodium hydroxide was added to the adsorbent. The mixture was stirred at 5 rpm to contact them for 2 minutes. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, α-amylase, β-amylase and glucoamylase were 0 units/ml, 1.31 units/ml and 2.06 units/ml, respectively. Thus, 0 unit (recovery rate, 0%) of α-amylase, 7.84 units (40.0%) of β-amylase and 12.35 units (95%) of glucoamylase could be recovered.

Further in the solution, any protease activity was not detected and neither coloration nor odor was noted. Furthermore, amounts of organic and inorganic materials in the solution were reduced to 1.7% and 1.3%, respectively, based on the contents in the raw solution. From the foregoing, glucoamylase in the raw solution could be selectively concentrated to about 9.5 times and purified.

EXAMPLE 10

Isolation and Purification of β-Amylase and Glucoamylase Using Cross-linked Maltohexose To 10 g of dry powders of maltohexose was added 90 ml of water. The mixture was heated to 50° C. with stirring to dissolve the powders. To the solution was added 33 ml of 4N sodium hydroxide. The mixture was charged in a 200 ml reaction flask equipped with a stirrer and a reflux condenser.

Then, 150 ml of epichlorohydrin was added to the mixture followed by heating at 80° C. for 6 hours with stirring at 20 rpm.

After completion of the reaction, the content was cooled to room temperature and the gelled product in the lower aqueous phase was filtered. To the gelatinous product was added 50 ml of ethanol. After stirring the gelatinous product was filtered and recovered.

The recovered gel was again suspended in 50 ml of ethanol. The suspension was filtered to recover the gelatinous product. This operation was repeated further 3 times. Next, the gelationous product was suspended in 50 ml of distilled water and isolated by filtration.

After repeating this operation 3 times, the matter was again dispersed in 50 ml of ethanol. The dispersion was filtered. After drying, the gelatinous product was ground into powders to give 9.7 g of white powders.

The solubility of the powders in water at 60° C. was 0.002 g or less, based on 100 g of water. After further immersing the powders in water of 60° C. for a day, a weight ratio of the hydrated gel to the powders was 13.5.

On the other hand, 20 ml of a culture filtrate (containing 0.50 units/ml of α-amylase, 0.98 units/ml of β-amylase and 1.30 units/ml of glucoamylase) of Aspergillus oryzae IFO-4176 was cooled to 6° C. and 0.2 g of the adsorbent powders described above was added thereto. The mixture was stirred at 5 rpm for 2 minutes.

The mixture was filtered and, α-amylase activity, β-amylase activity and glucoamylase activity in the filtrate were measured.

The respective enzyme activities in the supernatant were measured. In the supernatant, α-amylase, β-amylase and glucoamylase were 0.50 units/ml, 0.20 units/ml and 0.03 units/ml, respectively.

The amount of each enzyme adsorbed to the adsorbent described above was calculated as a value obtained by subtracting an enzyme concentration after the contact with the adsorbent from an enzyme concentration prior to the contact. As a result, α-amylase, β-amylase and glucoamylase were adsorbed to the adsorbent by 0 unit/ml, 0.88 units/ml and 1.27 units/ml, of the culture filtrate, respectively.

Accordingly, α-amylase present in the culture filtrate was not adsorbed but, 90% of β-amylase and 98% of glucoamylase were adsorbed to the absorbent.

Next, the adsorbent to which the aforesaid enzymes had been adsorbed was put in a container of 20 ml and 4 ml of a solution adjusted to pH 8.2 with sodium hydroxide was added to the adsorbent. The mixture was stirred at 5 rpm to contact them for 2 minutes. After centrifugation at 3000 rpm for 5 minutes, the mixture was separated into the adsorbent and the supernatant. Further 2 ml of water was added to the adsorbent to suspend it. The suspension was again centrifuged at 3000 rpm for 5 minutes to separate into the rinsing solution and the adsorbent by solid-liquid separation. The supernatant and rinsing solution obtained above were combined to give 6 ml of the enzyme-desorbed solution.

The enzyme concentrations in the enzyme-desorbed solution described above were measured. As a result, α-amylase, β-amylase and glucoamylase were 0 units/ml, 25.5 units/ml and 41.7 units/ml, respectively. Thus, 0 unit (recovery rate, 0%) of α-amylase, 15.3 units (78.0%) of β-amylase and 25.0 units (96.0%) of glucoamylase could be recovered.

Further in the solution, any protease activity was not detected and neither coloration nor odor was noted. Furthermore, amounts of organic and inorganic materials in the solution were reduced to 1.8% and 1.9%, respectively, based on the contents in the raw solution. From the foregoing, glucoamylase in the raw solution could be selectively concentrated to about 19.2 times and purified.

EXAMPLE 11

Isolation and Purification of Glucoamylase Using Cross-linked Glycogen Treated With Glucoamylase and α-Amylase To 5 g of dry powders of glycogen (estimated molecular weight, $4 \times 10^5$; estimated branching degree, 25%) prepared from Esherichia coli cells was added 95 ml of 0.05M sodium acetate buffer(pH 5.0). The mixture was heated to 70° C. with stirring to dissolve the powders. The solution was cooled to 50° C. Thirty milliliters of the solution was taken and, 2 ml of an α-amylase and glucoamylase solution mixture in which 200 units of glucoamylase derived from Aspergillus oryzae IFOr4176 had been dissolved, was added to the solution. The mixture was kept at 50° C.

The amount of glucose produced 2 hours later was measured and as a result, it reached approximately 70% based on the number of the glucose residues in the glycogen molecule tested. At this point, the molecular weight was $1 \times 10^5$.

The solution was packed in a cellophane tube for dialysis and dialyzed to 5 l of water at 8° C. for 17 hours. The content was freeze dried to give 0.85 g of white powders. A mean polymerization degree of the branched chains of the powders was determined to be 3.6.

To the powders was added 10 ml of water. The mixture was heated to 70° C. with stirring to dissolve the powders and make a viscous solution. Next, 35 ml of 6N sodium hydroxide was added to the solution. The mixture was charged in a 200 ml reaction flask equipped with a stirrer and a reflux condenser. Then, 150 ml of epichlorohydrin was added to the mixture followed by heating at 70° C. for 5.2 hours with stirring at 20 rpm.

After completion of the reaction, the content was cooled to room temperature and the gelled product in the lower aqueous phase was filtered.

To the gelatinous product was added 50 ml of ethanol. After stirring the gelatinous product was filtered and recovered. The recovered gel was again suspended in 50 ml of ethanol. The suspension was filtered to recover the gelatinous product. This operation was repeated further 3 times. Next, the gel-like product was suspended in 50 ml of distilled water and isolated by filtration. After repeating this operation 3 times, the matter was again dispersed in 60 ml of ethanol. The dispersion was filtered. After drying, the gelatinous product was ground into powders to give 0.7 g of white powders.

The solubility of the powders in water at 60° C. was 0.001 g or less, based on 100 g of water. After further immersing the powders in water of 60° C. for a day, a weight ratio of the hydrated gel to the powders was 14.1. By measurement of the non-reducing end of the powders, a mean polymerization degree of the branched chains was determined to be 2.9. Next, the following experiment was performed to see adsorption property of glucoamylase to the powders.

Forty milliliters of a culture filtrate (containing 0.50 units/ml of α-amylase, 0.98 units/ml of Aspergillus oryzae IFO-4176 was cooled to 6° C. and 0.2 g of the adsorbent powders described above was added thereto. They were contacted with each other by mixing for 2 minutes at 5 rpm. The content was filtered through a column (10 $\phi \times 50$ mm) equipped with a filter at the bottom thereof and, α-amylase activity, β-amylase activity and glucoamylase activity in the filtrate were measured.

In the supernatant, α-amylase, β-amylase and glucoamylase were 0.50 units/ml, 0.06 units/ml and 0.013 units/ml, respectively. The amount of each enzyme adsorbed to the adsorbent described above was calculated as a value obtained by subtracting an enzyme concentration after the contact with the adsorbent from an enzyme concentration prior to the contact. As a result, α-amylase present in the culture filtrate was not substantially adsorbed but 3.1% (0.95 units/ml) of β-amylase and 98% (0.013 units/ml) of glucoamylase were adsorbed to the adsorbent.

Next, 0.5M sodium chloride aqueous solution, which had been adjusted with a sodium hydroxide solution to pH 7.5, was flown through the column to which the aforesaid enzymes had been adsorbed and the effluent was recovered. Thereafter, 2 ml of water was flown to rinse the column. The rinsing liquid and the effluent described above were combined to give 6 ml of the enzyme-desorbed solution.

The enzyme concentrations in the enzyme-desorbed solution described above were measured. As a result, no α-amylase was detected but β-amylase and glucoamylase were 1.41 units/ml and 8.42 units/ml, respectively. By multiplying the concentrations of respective enzymes in the desorbed solution by 6 ml of the amount of solution, respective recovery amounts were determined to be 0 unit of α-amylase, 8.5 units of β-amylase and 50.5 units of glucoamylase. Thus, among the enzymes present in the raw solution, 0% of α-amylase, 3.6% of β-amylase and 91.0% of glucoamylase could be recovered by the adsorption and desorption of this example. Further in the solution, any protease activity was not detected and neither coloration nor odor was noted. Furthermore, amounts of organic and inorganic matters in the solution were reduced to 0.86% and 1.1%, respectively, based on the contents in the raw solution. By the use of the instant adsorbent, α-amylase and β-amylase can be selectively separated into the filtrate and glucoamylase selectively into the effluent from the adsorbent.

With respect to the effluent, glucoamylase was concentrated to 6.5 times based on the raw solution, whereas β-amylase was diluted to 2.5 times.

COMPARATIVE EXAMPLE 1

Isolation and Purification of Glucoamylase and β-Amylase Using Amylose

Forty milliliters of a culture filtrate (containing 0.50 units/ml of α-amylase, 0.98 units/ml of β-amylase and 1.30 units/ml of glucoamylase) of Aspergillus oryzae IFO-4176 of the same lot as in the examples was cooled to 6° C. and 0.2 g of the adsorbent powders described above was added thereto. They were contacted with each other by mixing for 2 minutes at 5 rpm. The mixture was filtered and, α-amylase activity, β-amylase activity and glucoamylase activity in the filtrate were measured.

In the supernatant, α-amylase, β-amylase and glucoamylase were 0.02 units/ml, 0.96 units/ml and 1.29 units/ml, respectively. The amount of each enzyme adsorbed to the amylose powders described above was calculated as a value obtained by subtracting an enzyme concentration after the contact with the amylase from an enzyme concentration prior to the contact. As a result, 96% (0.48 units/ml) of α-amylase and 2% (0.02 units/ml) of β-amylase were adsorbed and, glucoamylase was 1% (0.01 unit/ml), indicating that the enzymes other than α-amylase were not substantially adsorbed.

COMPARATIVE EXAMPLE 2

Isolation and Purification of β-Amylase and Glucoamylase by Applying Salting Out and Chromatography Ammonium sulfate was portionrwise added to 40 ml of of a culture filtrate (containing 20 units/ml of α-amylase, 0.5 units/ml; 39 units of β-amylase, 0.98 units/ml; 52 units of of glucoamylase, 1.3 units/ml) of Aspergillus oryzae IFO-4176 at 6° C. with stirring. The final concentration was made 12% (W/W) followed by stirring for 30 minutes. The solution was centrifuged at 3000 rpm for 5 minutes, whereby precipitates of amylase activity-free impurities were removed by sedimentation and the supernatant was recovered as an enzyme fraction. Ammonium sulfate was further added to the supernatant so as to become 35% (W/W) thereby to precipitate the 3 enzymes described above. The precipitates were centrifuged and recovered. The activities in the precipitates were 7.5 units of α-amylase, 7.2 units of β-amylase and 17 units of glucoamylase. Ammonium sulfate was further added to the centrifuged supernatant to make 40% solution close to the solubility of ammonium sulfate. However, no amylase activity was recognized in the formed precipitates; amylases were still dissolved but it was impossible to recover as precipitates by salting out.

Next, the precipitates described above were dissolved in 5 ml. The solution was adsorbed to a diethylaminoethyl cellulose column ($\phi$ 10×70 mm). While increasing a salt concentration in 0.05M Tris-amino-methane hydrochloride buffer, pH 6.0, from 0 to 1M with a linear gradient, the enzymes were eluted with the buffer. Eluted fractions, 150 ml, containing any of the 3 enzymes were fractionated and enzyme activities in the solution were measured. α-Amylase, β-amylase and glucoamylase were 4.8 units, 9.8 units and 11.3 units, respectively. Accordingly, among the enzymes present in the raw solution, 24% of α-amylase, 25% of β-amylase and 19% of glucoamylase could be recovered by the purification operation in this comparative example, in their activity amounts. Neither coloration nor odor was noted. An amount of high molecular organic matters in the solution was reduced to 3.5%, based on the content in the raw solution. The salt concentration was increased to 7.2 times. With respect to the respective enzyme concentrations of purified enzyme solution, α-amylase became 1/16 times, and β-amylase became 1/15 times and 1/20 times, based on the respective enzymes in the raw solution.

What we claim is:

1. A method for isolation and purification of one or both of microorganism-derived glucoamylase and microorganism-derived β-amylase which comprises the steps of:

contacting a crude enzyme aqueous solution containing one or both of microorganism-derived glucoamylase and microorganism-derived β-amylase with a three-dimensional, cross-linked high molecular weight substance which is obtained by cross-linking an α-1,4-linked glucose homooligomer intermolecularly by use of an epilialogen or by cross-linking intermolecularly or intramolecularly and intermolecularly glycogen or amylopectin having branched chains which have been previously treated with an amylase to shorten the branched chains, thereby to adsorb one or both of the microorganism-derived glucoamylase and microorganism-derived β-amylase forming a hydrated gel;

separating from said solution said hydrated gel of the three-dimensional, cross-linked high molecular weight substance to which one or both of microorganism-derived glucoamylase and microorganism-derived β-amylase have been adsorbed;

contacting said hydrated gel with a weakly alkaline aqueous salt solution of at least 0.5M to desorb and or both of said adsorbed microorganism derived glucoamylase and microorganism derived β-amylase amylase; and recovering one or both of said desorbed microorganism derived glucoamylase and microorganism-derived β-amylase.

2. A method according to claim 1, wherein said crude enzyme aqueous solution contains α-amylase as a contaminant.

3. A method according to claim 1 or 2, wherein said three-dimensional, cross-linked high molecular weight substance is one obtained by cross-linking intermolecularly an α-1,4-linked glucose homooligomer having a mean polymerization degree of 1 to 6 and glucoamylase is selectively adsorbed on the high molecular weight substance.

* * * * *